United States Patent [19]

Froehler et al.

[11] Patent Number: 4,959,463

[45] Date of Patent: Sep. 25, 1990

[54] INTERMEDIATES

[75] Inventors: Brian C. Froehler, Belmont; Mark D. Matteucci, Redwood City, both of Calif.

[73] Assignee: Genentech, Inc., South San Francisco, Calif.

[21] Appl. No.: 910,048

[22] Filed: Sep. 19, 1986

Related U.S. Application Data

[63] Continuation-in-part of Ser. No. 787,280, Oct. 15, 1985, abandoned.

[51] Int. Cl.$^5$ .................... C07H 19/06; C07H 19/16; C07H 21/04; C07H 21/02
[52] U.S. Cl. ........................................ 536/27; 536/28; 536/29
[58] Field of Search ............................. 536/27, 28, 29

[56] References Cited

U.S. PATENT DOCUMENTS

| | | | |
|---|---|---|---|
| 3,687,808 | 8/1972 | Merigan et al. | 536/27 |
| 4,458,066 | 7/1984 | Caruthers et al. | 536/27 |
| 4,469,863 | 12/1980 | Ts'o et al. | |
| 4,507,433 | 7/1983 | Miller et al. | |
| 4,547,569 | 10/1985 | Letsinger et al. | 536/29 |
| 4,725,677 | 2/1988 | Köster et al. | 536/27 |

FOREIGN PATENT DOCUMENTS

| | | |
|---|---|---|
| 3275684 | 6/1983 | Australia . |
| 2476092 | 2/1980 | France . |
| 84-01778 | 5/1984 | PCT Int'l Appl. . |
| 2125798 | 8/1982 | United Kingdom . |
| 2153356 | 8/1985 | United Kingdom . |

OTHER PUBLICATIONS

Nelson et al., J. Org. Chem., vol. 49, pp. 2314–2317 (1984).
Eckstein et al., Eur. J. of Bio chem., vol. 13, pp. 558–564, 1970.
Lee et al., Biochemistry, vol. 24, pp. 551–555, 1985.
Athirston et al., J. Chem. Soc., pp. 660–663, 1945.
Moffett et al., J. Scs, vol. 83, pp. 649–658, 1961.
Nemer et al., (I), Tetrahedron Letters, vol. 21, pp. 4153–4154, 1980.
Nemer et al. (II), Tetrahedron Letters, vol. 21, p0p. 4149–4152, 1980.
Garegg et al. (I) Chemica Scpyta, vol. 25, pp. 280–282 (1985).
Garegg et al. (II), Chemica Scripta, vol. 26, pp. 59-62, (1962), Note Ref. to Oral Presentation, 8/85 on p. 59.
Garegg et al. (III), Tetrahedron Letters, vol. 27, pp. 4055–4058, 1986.
Garegg et al. (IV), Tetrahedron Letters, vol. 27, pp. 4051–4054, 1986.
Fujii et al., Tetrahedron Letters, vol. 26 (No. 8), 935–938 (1986).
Hsu et al., J. Chem. Soc., 19576, pp. 3291–3296.
Kume et al., J. Org Chem., 49, pp. 2139–2143.
DeClercq et al., Virology, 42:421–428 (1970).
Alvardo-Urbina et al., Science, 214:270–274 (1981).
Garegg et al., *Chemica Scripta* 25, 280 (1985).
Garegg et al., *Chemica Scripta* 26, 59 (1985).
Garegg et al., *Tetrahedron Letters* 27, 4055 (1986).
Garegg et al., *Tetrahedron Letters* 27, 4051 (1986).

*Primary Examiner*—John W. Rollins
*Assistant Examiner*—L. Eric Crane

[57] ABSTRACT

A method is provided for the high fidelity, rapid and economical in vitro synthesis of oligonucleotides. Nucleoside H-phosphonates are condensed in seriatim using a dehydrating agent to produce a poly (nucleoside H-phosphonate). The produce is oxidized to yield the desired oligonucleotide. A novel reagent is provided for multiple nucleoside additions in single cycles.

25 Claims, No Drawings

INTERMEDIATES

This is a continuation-in-part of U.S. Ser. No. 787,280. filed Oct. 15, 1985, now abandoned.

This invention relates to the in vitro synthesis of oligonucleotides. In particular it relates to the preparation of deoxyoligonucleotides for use in recombinant host-vector systems and as intermediates in the preparation of labelled oligonucleotide probes for diagnostic assays Oligonucleotides are presently prepared in vitro by one of two prevalent methods, the phosphoramidite method (for example see Adams et al., 1983, "J. Amer. Chem. Soc." 105: 661 and Froehler et al., 1983 "Tetrahedron Lett." 24. 3171) or the phosphotriester route (German Offenlegungsshrift No. 2644432). Both methods, while efficient and widely accepted, employ large amounts of costly monomer. These methods are also complex. The phosphoramidite method requires an aqueous oxidation step after each condensation, while the triester method requires that the aborted subpopulation of oligonucleotides (those that have not had a monomer added during a cycle) be "capped" in a separate step in order to prevent further chain elongation of the aborted oligonucleotides in future cycles. It is an object of this invention to provide a method for the oligonucleotide synthesis that is more economical and reliable than the methods currently available.

It is known to prepare nucleoside phosphonates by condensation of nucleosides with phosphorous acid using aryl sulfonyl chloride (Sekine et al., 1979; "Tetrahedron Lett." 20: 1145), or carbodiimides (Schofield et al , 1961, "J. Am. Chem. Soc." page 2316). Hall et al. ([1957], "J. Chem. Soc." Nucleotides Part XLI, pp 3291–3296) further treated the nucleoside H-phosphonate to prepare the corresponding dinucleotide phosphonate using diphenylchlorophosphate followed by oxidation to produce the corresponding dinucleotide phosphate. Thus, notwithstanding knowledge in the art relating to the preparation of dinucleotide phosphate since 1957, and the intervening development of two complex and costly methodologies for the in vitro preparation of oligonucleotides, the Hall et al. disclosure has remained unexploited for the preparation of oligonucleotides.

Garegg et al., "Chemica Scripta" 25: 280–282 (1985) found that 5'-O-dimethoxytritylthymidine 3'-hydrogenphosphonate reacts rapidly with 3'-O-benzoylthymidine in the presence of an activator such as diphenylphosphorochloridate (also known as diphenylchlorophosphate), 2,4,6-triisopropylbenzenesulfonyl chloride or 2,4,6-triisopropyl-benzenesulfonyl tetrazolide to form, in quantitative yield, a phosphonate diester bond. According to Garegg et al., the stability of the 3'-phosphonates when compared to the corresponding 3'-phosphoramidites, together with their comparable reactivity to phosphoramidites on activation, made them suitable as starting materials for oligonucleotide synthesis. The Garegg activating agents have been found by the inventors herein to be unsuitable for practical oligonucleotide synthesis because of the poor yields so obtained, a discovery that may help to explain the three decades that have passed without the art having harnessed phosphonate chemistry to the objective of oligonucleotide synthesis.

The synthesis of DNA containing internucleotide phosphate analogues is becoming a field of great interest. Miller and Ts'o have shown that methyl phosphonate analogues of DNA readily pass through cell membranes and inhibit protein synthesis, presumably by interfering with mRNA translation (Blake et al., Biochemistry 24, 6139 (1985), Smith et al., Proc. Natl. Acad. Sci. 83, 2787 (1986)). Phosphoramidate analogues of dinucleotides are known to bind to complementary polynucleotides and can be used for the attachment of various ligands to DNA (Letsinger et al , Nucl. Acids Res. 14, 3487 (1986)). Oxidation of dinucleoside H-phosphonates in the presence of amines leads to the corresponding dinucleotide phosphoramidates (Nemer et al., Tetrahedron Lett. 21, 4149 (1980), Atherton et al., J. Chem. Soc. 660 (1945)) in high yield. Methods are needed for the facile preparation of phosphoramidate, thiophosphate and phosphate triester analogues of oligonucleotides.

SUMMARY

The objectives herein are accomplished by a method for synthesizing a polynucleotide which comprises (a) providing a nucleoside bound to a carrier, (b) condensing a blocked nucleoside H-phosphonate with the 5' hydroxyl of the carrier-bound nucleoside in the presence of a dehydrating agent, (c) removing the 5' blocking group of the nucleoside H-phosphonate of step (b), (d) sequentially repeating steps (b) and (c) using selected nucleoside H-phosphonates until a polynucleotide H-phosphonate having greater than two nucleotides has been obtained, (e) oxidizing the polynucleotide H-phosphonate to form the corresponding polynucleotide, and (f) separating the polynucleotide from the carrier. The polynucleoside H-phosphonates are useful as starting materials for the novel synthesis of the phosphoramidate, thiophosphate and phosphate triester oligonucleotides.

DETAILED DESCRIPTION

The starting materials for the practice of the inventive method comprise a carrier-bound nucleoside and blocked nucleoside H-phosphonate monomers. The 5' hydroxyl of the carrier bound nucleoside is not blocked. The nucleosides employed herein are the monomers of RNA or DNA or their derivatives. Exemplary ribose-containing nucleosides include adenosine, guanosine, inosine, cytidine, thymine ribonucleoside, and uridine. Deoxyribose-containing nucleosides include deoxyadenosine, deoxycytidine, deoxyguanosine, and thymidine. The first group of nucleosides are used in synthesizing mRNA or tRNA, the second group in preparing DNA.

The preferred blocked nucleoside H-phosphonate monomers are analogues of the nucleotides constituting nucleic acids. The blocking groups generally are triphenylmethyl ethers of the ribose or deoxyribose hydroxyl substituents. Their function is to restrict the condensation reaction to the 5' hydroxyl of the carrier-bound nucleoside or oligonucleotide. The preferred starting phosphonates for the preparation of oligodeoxynucleotides and their corresponding nucleosides, designated parenthetically, are 5'dimethoxytrityl-3'-thymidine H-phosphonate (thymidine) 5' dimethoxytrityl-3'-[N$^6$-benzoyldeoxyadenosine] H-phosphonate (deoxyadenosine), 5' dimethoxytrityl-3'-[N$^4$-benzoylcytidine] H-phosphonate (deoxycytidine), and 5' dimethoxytrityl-3'-[N$^2$-isobutyl deoxyguanosine] H-phosphonate (deoxyguanosine). The starting materials for the preparation of oligoribonucleotides are similar, for example for adenosine, 5'dimethoxytrityl-2'-dimethyl t-butyl silyl-[N⁶-benzoyladenosine]-3' H-phosphonate. The starting phosphonates are prepared by methods known per se. For example, see Sekine et al., "Tetr. Lett." 16, 1711 (1973). Another method for preparing the starting phosphonates (which is preferred) employs tris (1, 2, 4-triazolyl) phosphite (TTP). TTP is conveniently generated in situ from phosphorus trichloride ($PCl_3$), 1, 2, 4-triazole and N-methyl morpholine in anhydrous methylene chloride ($CH_2Cl_2$).

Carriers are selected that are insoluble in the reagents used for the oligonucleotide synthesis, this being for convenience in recovering the polynucleotide after each condensation cycle. The carrier also is sufficiently porous to permit the facile entry of reactants and elution of product and reactants. A preferred carrier is controlled pore glass, although silica gel or polystyrene also are acceptable. Carrier-bound nucleosides are prepared by known procedures, for example Chow et al., "Nucl. Acids Res." 9: 2807 (1981).

Nucleoside H-phosphonates exist as an anion having a positively charged counterion. Triethyl ammonium (TEAH⁺) or 1,8 Diazabicyclo [5.4.0] undec-7eneonium (DBUH⁺) are preferred counterions. The DBUH salts of phosphonates have increased stability in anhydrous solvents.

The carrier bound nucleoside and the nucleoside 3' H-phosphonates are selected in seriatim so as to correspond to the predetermined sequence of the oligonucleotide to be synthesized, with the 3' nucleoside being carrier-bound. Oligonucleotide chain elongation proceeds in conformance with this predetermined sequence in a series of condensations, each one of which results in the addition of another nucleoside to the oligomer.

In the first of these condensations, the carrier-bound nucleoside is condensed with the second nucleoside in the oligonucleotide. The key reagent in this reaction as well as in the subsequent condensations is the dehydrating agent. Suitable dehydrating agents generally fall within the classes of phosphorylating agents or acylating agents and include isobutyl chloroformate, diphenyl chlorophosphate, organic acid anhydrides such as acetic anhydride, isobutyric anhydride and trimethylacetic anhydride, and organic acid halides such as pivaloyl chloride, pivaloyl bromide and benzoyl chloride. Diphenylchlorophosphate, carbodiimides, aryl sulfonyl chlorides and aryl sulfonyl tetrazolides in our experience result in extremely poor yields. The property of the acylating or phosphorylating agent that is most important for the purposes of preparing oligonucleotides is its ability to add a nucleoside to substantially all of the nascent carrier-bound chains at each cycle. If the additional nucleoside is not added to a subpopulation of chains, i.e. a cycle is aborted as to that subpopulation, then the resulting oligonucleotide generated by further addition to that subpopulation will be one base short. This will destroy the utility of the oligonucleotide as a component in DNA which is to be expressed in recombinant culture because the deletion will shift the DNA out of reading frame, and it is difficult to detect contaminating deletion mutants in long oligonucleotide products. Thus, when preparing oligonucleotides for use in molecular biology it is important to select a dehydrating agent that exhibits high fidelity in chain elongation, i.e., high yield addition at each cycle. Selecting such superior agents other than those specifically set forth herein is accomplished by the use of a screening assay.

The screening assay to be employed is described in more detail in Example 2. A nucleoside H-phosphonate(N) is condensed to a carrier-bound nucleoside through four cycles, the last one of which should yield $N_5$, then the polynucleotide H-phosphonates are separated from the carrier, converted to the oligonucleotides and separated on HPLC in order to determine the distribution of oligomers from $N_2$ to $N_5$. If the selected dehydrating agent produces an oligomer mixture having greater than about 80 mole % of $N_5$ as measured by spectrophotometric adsorption corrected for the extinction coefficients of the oligomers, and usually greater than about 90%, then the agent will be considered preferred for the purposes of this invention. Alternatively, the dehydrating agent that is selected is one which, after 49 cycles of step (d) followed by steps (e) and (f), yields an oligonucleotide composition wherein the desired 50 nucleotide oligonucleotide in the composition is present in a greater molar amount than any other oligonucleotide species in the composition. The agents used by the art for the preparation of dinucleosides have been phosphorylating or sulfonylating agents. Agents of these classes used by the art are not capable of meeting the rigorous standards herein, particularly diphenyl chlorophosphate, 2,4,6-triisopropylbenzenesulfonyl chloride or 2,4,6-triisopropylbenzene sulfonyl tetrazolide.

The preferred activating agents are acylating agents. Particularly preferred are acylating agents having the structure

wherein A is aryl or

in which the R groups are inert substituents preferably selected from the group of the same or different normal or branched alkyl, aryl, heteroalkyl or heteroaryl, and X is halogen or a pseudo-halogen, e.g. a heterocyclic secondary amine or an active ester. R is preferably alkyl, X is preferably chloride or bromide. Pivaloyl chloride, wherein R is $CH_3$ and X is Cl, is the preferred acylating agent.

A representative heterocyclic amine X group is tetrazole. A typical example of this species is

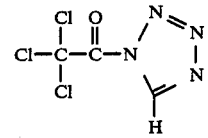

It is produced in accord with methods known per se wherein

is reacted with tetrazole.

A representative active ester is

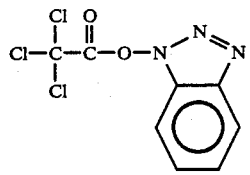

produced by the reaction of

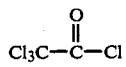

with hydroxybenztriazole. Other suitable leaving groups will be apparent to the artisan.

The dehydrating agent typically is employed at a concentration of about 25 to 100 mM. Pivaloyl chloride preferably is present in a concentration of about 50 mM or 5 molar equivalents of pivaloyl chloride relative to the phosphonate monomer. The use of 10 equivalents reduced the yield of oligonucleotide, thus indicating that competitive acylation is yield limiting and that no extraneous capping step is required. The pivaloyl chloride reacts with the small proportion of aborted chains to produce a pivolate ester that is incapable of participating in further condensations. Thus, incomplete chains are capped without any need to introduce a separate step or additional reagents.

The quantity of phosphonate required in the condensation generally ranges about from 5 mM to 20 mM, ordinarily about 10 mM (~5 eq. relative to the 5'-OH component). This is considerably less than the amount of monomer employed in known oligonucleotide synthetic processes, which typically require about 50 mM.

The solvent for the condensation reaction is an anhydrous organic solvent, preferably anhydrous pyridine/acetonitrile in volume proportions of 1:1.

The reaction generally is conducted by mixing dehydrating agent and selected phosphonate solutions and then contacting the mixture with the carrier-bound oligonucleotide chain. Typically, the carrier is particulate and packed into a column over which the solution of monomer and dehydrating agent then is passed. The contact time generally is about from 0.5 to 5 minutes, with about 1.5 minutes being preferred. The reaction temperature is about from 10° C. to 30° C. preferably 20° C.

The solution containing the residual dehydrating agent and nucleoside H-phosphonate is removed from the carrier after each cycle by washing with an organic solvent such as acetonitrile. Thereafter, the protecting group is removed from the added nucleoside, preferably by treatment with a 2.5% vol/vol dichloroacetic acid/$CH_2Cl_2$ solution, although 1% w/v trichloroacetic acid/$CH_2Cl_2$ or ZnBr-saturated nitromethane also are useful. Other deprotection procedures suitable for other known protecting groups will be apparent to the ordinary artisan. Then the carrier preferably is washed with anhydrous pyridine/acetonitrile (1/1, vol/vol) and the condensation reaction is repeated in as many additional cycles as are required to prepare the predetermined oligonucleotide.

After the required number of synthetic cycles the polynucleotide H-phosphonate is oxidized to the nucleic acid. In order to prepare oligonucleotides having phosphoramidate internucleotide linkages, the oxidation is conducted in the presence of a primary or secondary amine and, preferably carbon tetrachloride. The preferred oxidizing agent is aqueous iodine to generate phosphate diesters into nucleotide linkages. Other representative oxidizing agents include N-chlorosuccinimide, N-bromosuccinimide, or salts of periodic acid. Thereafter, the oligonucleotide is separated from the carrier, in the preferred instance by incubation with concentrated ammonium hydroxide followed by filtration to remove the residual silica gel and evaporation of the oligonucleotide-containing solution. If desired the oligonucleotide then is purified by HPLC, polyacrylamide gel electrophoresis or other conventional techniques and the fidelity of the product confirmed by nucleic acid sequence analysis.

While the foregoing discussion has revolved around the consecutive addition of mononucleoside phosphonates it will be understood that more than one nucleoside can be added in a given cycle by using poly (nucleoside phosphonates), generally di- or trinucleoside phosphonates. These reagents are readily prepared by condensing a soluble nucleoside (which may or may not be bound to a carrier) to a nucleoside phosphonate otherwise as described above for chain initiation. Such dinucleoside diphosphonates are then employed in place of the mononucleoside phosphonates, or to prepare other poly(nucleoside phosphonates). These novel intermediates have the structure

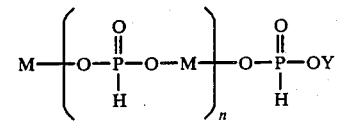

wherein Y is a counterion such as $DBUH^+$, n is 1 or greater than 1, ordinarily 2, and M is a nucleoside. Ordinarily the nucleoside will be protected. An example is 5' Dimethoxytrityl-3'-thymidyl-5'-H-phosphonate-3'-thymidine-H-phosphonate. These agents should be purified and stored as anhydrous solids.

The following examples are illustrative of the invention but are not to be considered as limitations on its scope, which is defined by the appended claims.

EXAMPLE 1

Preparation of Eicosathymidylic Acid (T20) and Tetracontathymidylic Acid (T40)

The synthetic utility of 5'-dimethoxytrityl-3'-thymidine-H-phosphonate 1 demonstrated by the synthesis of $T_{20}$ and $T_{40}$ on silica gel. 5'-Dimethoxytrityl-3'-thymidine H-phosphonate was prepared as previously described and characterized by $^{31}P$ NMR (δ-0.27 ppm, J (P-H)=605 Hz) ($^{31}P$ NMR spectra were obtained in an anhydrous Pyr/$CH_3CN$ (1/1) solution and chemical shifts are reported relative to 5 percent phosphoric acid/$D_2O$ (external standard)). The reaction scheme (scheme 1) was as follows, wherein DMT is dimethoxytrityl, pyr is pyridine, DCA is dichloroacetic acid and R is succinyl silica.

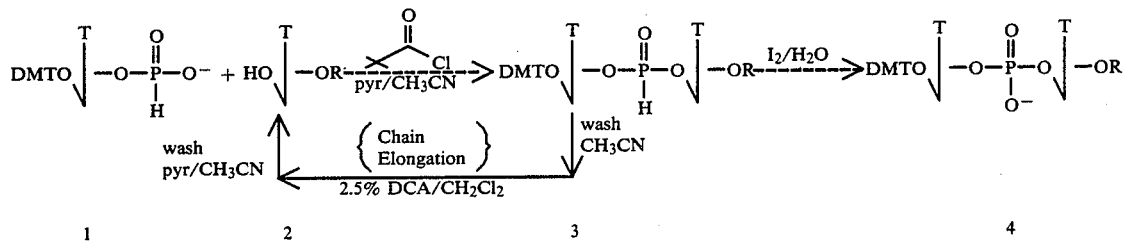

The polymer support (silica gel) was derivatized to 25 μmole 3'-succinyl thymidine per gram of silica gel as previously described (Chow et al., Id). The synthetic cycle consisted of a condensation reaction of 2 with 10 mM 1 (~5 eq. relative to 5'-OH component 2) and 50 mM pivaloyl chloride at 20° C. in anhydrous pyridine/acetonitrile (1/1) for 5 min, followed by dimethoxytrityl deprotection of 3 using 2.5% DCA/CH$_2$Cl$_2$ (2 min). After the required number of synthetic cycles, the polythymidine H-phosphonate product 3 was oxidized to polythymidylic acid 4 with 0.2M I$_2$ in tetrahydrofuran/Pyr/H$_2$O (90/5/5) (5 min). The product 4 was removed from the solid support (conc. NH$_4$OH/5 hr./55° C.) and evaporated. HPLC analysis of the crude product T$_{20}$ demonstrated that the product peak co-eluted with a T$_{20}$ standard prepared by the phosphoramidite method. The T$_{20}$ and T$_{40}$ crude products also were evaluated by polyacrylamide gel electrophoresis and visualized by U.V. shadowing. The analytical data clearly demonstrated the high yield synthesis of both T$_{20}$ and T$_{40}$. T$_{40}$ was further evaluated by 5'-end labeling with γ-$^{32}$P-ATP using polynucleotide T4 kinase followed by complete degradation with snake venom phosphodiesterase. By all criteria, the synthetic T$_{40}$ was comparable to a standard T$_{40}$.

EXAMPLE 2

Identification of Preferred Dehydrating Agent

The method of Example 1 was repeated except that parallel cycles were run with diphenyl chlorophosphate (DPCP) as the dehydrating agent and the reaction was only continued through 4 cycles to pentathymidylic acid (T$_5$). The crude column eluate was subjected to HPLC analysis to determine the percentage of oligonucleotides representing premature chain terminations. The HPLC resin was the Zorbax-NH$_2$ brand. The flow rate was 2.5 ml/min. of a linear gradient of 25 mM to 250 mM KH$_2$PO$_4$ in 15% vol/vol CH$_3$CN (pH 5.5). Fractions were collected over 15 min. and adsorbance measured at 254 nm. The heights of the single, substantially symmetrical peaks for each of T$_2$, T$_3$, T$_4$ and T$_5$ were taken from the HPLC charts and converted into percentages of total polythymidine in each crude eluate, correcting for the coefficient of extinction for each oligomer (by multiplying the peak values by 2.5, 1.75, 1.25, and 1 respectively). The results are shown in the following table.

| oligomer | Percent oligomer | |
|---|---|---|
| | DPDC | Pivaloyl chloride |
| T2 | 25 | 2.5 |
| T3 | 23 | 3.5 |
| T4 | 44 | 5 |
| T5 | 8 | 89 |

These results demonstrate that pivaloyl chloride is a preferred dehydrating agent, producing only about 11% of prematurely terminated oligomers through 4 cycles.

The yield of T5 using DPDC was only about 10% of that obtained by the use of pivaloyl chloride. Aryl sulfonyl chlorides and carbodiimides produced no detectable T5. Thus the method of this invention using the preferred acylating agents unexpectedly results in greater yields and reduces premature chain termination.

EXAMPLE 3

Preparation of Nucleoside H-Phosphonate

The following scheme was used to prepare deoxynucleosides for use herein.

Scheme 2

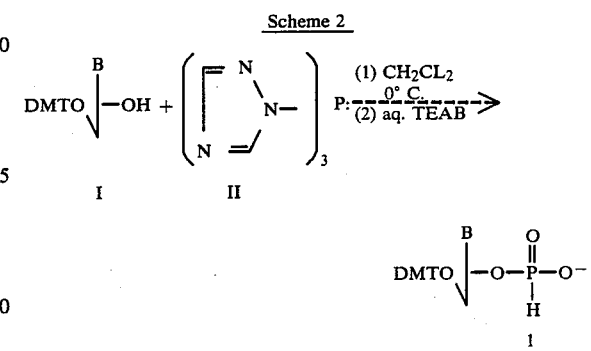

B =
(a) thymine
(b) N$^6$-benzoyl adenine
(c) N$^4$-benzoly cytosine
(d) N$^2$-isobutyryl guanine
(e) N$^6$-diisobutyl formamidine adenine To a stirred solution of PCl$_3$ (75 mmole) and N-methyl morpholine (750 mmole) in 750 ml anhydrous CH$_2$Cl$_2$ was added 1,2,4-triazole (250 mmole) at room temperature. After 30 min. the reaction mixture was cooled to 0° C. and 5'-Dimethoxytrityl thymidine (Ia, 15 mmole, dried by co-evaporation from CH$_3$CN) in 200 ml anhydrous CH$_2$Cl$_2$ was added dropwise over 20 min., stirred for 10 min., poured into 600 ml of 1.0M aqueous triethylammonium bicarbonate (TEAB, pH 8.5), shaken and separated. The aqueous phase was extracted with 200 ml CH$_2$Cl$_2$ and the combined organic phase was dried over Na$_2$SO$_4$ and evaporated to a foam. Silica gel column chromatography (2 percent Et$_3$N/CH$_2$Cl$_2$ —>2 percent Et$_3$N/10 percent MeOH/CH$_2$Cl$_2$) followed by TEAB extraction and evaporation yielded 5'-dimethoxytrityl-3'-thymidine H-phosphonate (1a) in 90 percent yield. All other deoxynucleoside H-phosphonates were prepared by the same procedure. Table 1 reports isolated yields and $^{31}$P NMR data:

TABLE 1

| Nucleoside H-phosphonate | $^{31}$P NMR[1] Chemical Shift | J(P-H) | Yield[2] (Percent) |
|---|---|---|---|
| thymidine (1a) | −0.3 ppm | 605 Hz | 90 |
| deoxyadenosine (1b) | −0.3 ppm | 600 Hz | 85 |
| deoxycytidine (1c) | −0.3 ppm | 603 Hz | 86 |
| deoxyguanosine (1d) | −0.6 ppm | 605 Hz | 77 |

[1] $^{31}$p NMR spectra were obtained in an anhydrous Pyr/CH$_3$CN (1/1) solution and chemical shifts are reported rlative to 5 percent phosphoric acid/$_2$O (external standard).
[2] Isolated yield based upon protected deoxynucleuside (Ia-d).

EXAMPLE 4

Synthesis of Deoxyoligonucleotides

This currently represents the best mode for practicing the invention. Syntheses were performed with a Biosearch Model 8600 DNA synthesizer. Trimethylacetyl chloride (pivaloyl chloride) was distilled at atmospheric pressure and stored under Argon (Ar). Pyridine (Pyr) was distilled from p-toluenesulfonyl chloride, then freshly distilled from calcium hydride. Acetonitrile (CH$_3$CN) was dried over activated 3 Angstrom molecular sieves. Deoxy-nucleoside H-phosphonates (1a-d) were dried by co-evaporation from anhydrous CH$_3$CN and reconstituted in anhydrous Pyr/CH$_3$CN (1/1). Syntheses were performed on control pore glass (0.1 μmole scale) using the following protocol.

| Synthetic Cycle (Scheme 1. Example 1) |
|---|
| (1) Wash - anhydrous CH$_3$CN (45 sec). |
| (2) Deblock - 2.5 percent dichloroacetic acid (DCA)/CH$_2$Cl$_2$ (1 min.). |
| (3) Wash - anhydrous Pyr/CH$_3$CN (45 sec). |
| (4) Couple - 10 mM deoxynucleoside H-phosphonate (1a-d), 50 mM pivaloyl chloride in anhydrous Pyr/CH$_3$CN (1/1 by vol) (1.5 min). |
| (5) Repeat steps 1-4 until the nucleotide sequence is complete. |
| (6) Deblock - 2.5 percent DCA/CH$_2$Cl$_2$ (1 min). |
| (7) Oxidize H-phosphonate DNA with: (1) 0.1 M I$_2$ in Pyr/NMI/H$_2$O/THF (5/1/5/90 by vol) (2.5 min), (2) 0.1 M I$_2$ in Et$_3$N/H$_2$O/THF (5/5/90 by vol) (2.5 min). The DNA was removed from the polymer, deprotected (conc. NH$_4$OH, 55° C., 5 hrs.) and evaporated. |

Deoxynucleoside H-phosphates (1a-b) have been used for the complete synthesis of deoxyoligonucleotides (DNA) up to 107 bases in length, although this is not an upper limit on synthetic capability. The synthetic protocol described above uses a minimal amount of deoxynucleoside H-phosphonate (2.5 mg/coupling) in a simplified and rapid procedure (4 min/cycle. The internucleoside phosphorus is protected from unwanted side reactions by its oxidation state and the native phosphate diester is generated after synthesis by aqueous I$_2$ oxidation.

Oxidation of a polymer bound polynucleoside H-phosphonate (3) with 0.1M I$_2$ in a Pyr/H$_2$O/THF (5/5/90) solution has been inadequate for consistent results. The aqueous I$_2$ oxidation of dialkyl H-phosphonates is subject to general base catalysis (Lewis, E. S. and Spears, L. G., J. Amer. Chem. Soc., 107, 3918 (1985)) and we have determined that addition of N-methyl imidazole (NMI) or stronger bases (i.e. N-methyl morpholine or triethylamine (Et$_3$N) increases the rate of oxidation and is essential for the oxidation of long deoxyoligonucleoside H-phosphonates (3, >40 bases). Dialkyl H-phosphonates are susceptible to alkaline hydrolysis (Kume, A., Fujii, M., Sekine, M. and Hata, T., J. Org. Chem., 49, 2139 [1984]) and we have observed that the aqueous oxidation of polynucleoside H-phosphates (3) using Et$_3$N is complicated by competitive hydrolysis. The I$_2$ oxidation of long deoxyoligonucleoside H-phosphonates (3), >40 bases) first with a weakly basic solution (Pyr/NMI) followed by oxidation with a strongly basic solution (Et$_3$N) gives the highest yield of product deoxyoligonucleotide (4). Additionally we have found that an aqueous I$_2$ solution disproportionates to IO$_3$− and I− (Lewis, Id. ) and an alkaline IO$_3$− solution will not oxidize a dinucleoside H-phosphonate (3) (Brown, D. M. and Hammond, P. R., J. Chem. Soc., 4229 [1960]). Therefore it is necessary to prepare separate solutions [A=0.2M I$_2$/THF, B=Base/H$_2$O/THF (1/1/8)] and mix them immediately prior to use for the consistent and rapid oxidation of deoxyoligonucleoside H-phosphonates (3).

Experiments were performed to evaluate the stability of the deoxyoligonucleoside H-phosphonate linkage (3) to the reagents used in deoxyoligonucleotide synthesis. A 24-mer was prepared and, prior to oxidation of the deoxynucleoside-H-phosphonate (3), aliquots of the solid support were treated for 4 hours with: (1) anhydrous Pyr/CH$_3$CN (1/1), (2) anhydrous CH$_3$CN, (3) 100 mM pivaloyl chloride in anhydrous Pyr/CH$_3$CN (1/1) and (4) 2.5 percent DCA/CH$_2$Cl$_2$, washed with CH$_3$CN, oxidized, washed, deprotected (conc. NH$_4$OH/5 hr./55° C.) and evaporated. After 5'-end labeling with γ-$^{32}$P-ATP using polynucleotide T4 kinase the samples were analyzed by gel electrophoresis and autoradiography (data not shown). Under these conditions no detectable degradation of the polynucleoside H-phosphonate (3) is observed, but addition of 1 percent H$_2$O to CH$_3$CN or the Pyr/CH$_3$CN solution leads to detectable degradation in the 4 hr. time period. These results indicate that the H-phosphonate linkage serves as a phosphorus protecting group throughout synthesis.

It has been shown that 3' or 5'-phosphate tiester stabilizes the glycosidic bond of deoxyadenosine to acid mediated depurination (Tanaka, T. and Letsinger, R. L., Nucl. Acids Res., 10, 3249 (1982)). The effect an internucleoside H-phosphonate linkage (3) would have on the rate of depurination was assessed. A polymer bound 3'-thymidine-5'-deoxyadenosine dinucleoside H-phosphonate, protected with a N$^6$-benzoyl amide (3b,a) or N$^6$-diisobutyl formamidine (3e,a), was treated with 2.5 percent DGA/CH$_2$Cl$_2$ for 24 hours and analyzed. No detectable difference in rate of depurination between the H-phosphonate diester (3) and the methyl phosphate triester was observed (data not shown). This experiment also confirmed the added stability of the N$^6$-amidine protected deoxyadenosine relative to the N$^6$-amidine deoxyadenosine.

Specific sequences of DNA were synthesized using the described protocol and the crude product characterized.

TABLE

Sequences of synthesized deoxyoligonucleotides

```
                        *1                              *2
                        ▼                               ▼
78a  5'-AGCTCTCGTAAAAAGGGTATCGACAATGAAAGCAATTTTCGTACTGAAAGGTTCACTGGA
78b  3'-      GAGCATTTTTCCCATAGCTGTTACTTTCGTTAAAAGCATGACTTTCCAAGTGACCT

*3
     ▼
     CGAATTCTGATTGAATGA    -3'
     GCTTAAGACTAACTTACTCTAG-5'

99   5'-AGTAGCAAGCTTGAGGTGTGGCAGGCTTGAGATCTGGCCATACATTGAGTGACAATGAC
       ATCCACTTTGCCTTTCTCTCCACAGGTGTCCACTCCCAG-3'

107a 5'-AATTCATGAAAAAGAATATCGCATTTCTTCTTGCATCTATGTTCGTTTTTTCTATTGCTA
107b 3'-     GTACTTTTTCTTATAGCGTAAAGAAGAACGTAGATACAAGCAAAAAAGATAACGAT

CAAACGCGTATGCAGACTCATGGATGGAGGAAGTTATTAAATTATGC    -3'
     GTTTGCGCATACGTCTGAGTACCTACCTCCTTCAATAATTTAATACGCCGG-5'
```

The deoxyoligonucleotides 78a, 78b and 99 were also synthesized with methoxy diisopropylamino phosphoramidites and are included in the Table for comparison. The amidite syntheses were carried out using a standard protocol except that a 30 second aqueous wash was incorporated prior to oxidation to hydrolyze possible phosphite-heterocyclic base adducts. The data presented in the Table clearly demonstrate the high yield synthesis of product deoxyoligonucleotides using deoxynucleoside H-phosphonate intermediates. At this time the sequence fidelity of H-phosphonate DNA is lower than that produced by phosphoramidites; however, this disadvantage is offset by a simpler synthetic cycle and significantly lower concentration of deoxynucleoside H-phosphonate required for synthesis.

EXAMPLE 5

The dinucleotide phosphoramidates 2e and 2f (Scheme 3) were initially prepared by oxidation of the polymer bound dinucleoside H-phosphonate 1

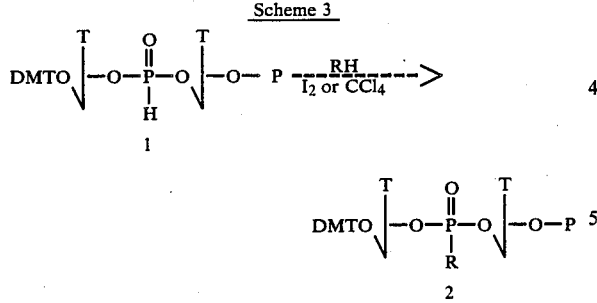

Scheme 3

RH =
(a) H$_2$O
(b) NH$_3$
(c) MeNH$_2$
(d) n-BuNH$_2$ (e) 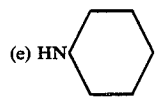

(f) HN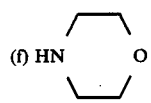O

-continued
Scheme 3

(g) HN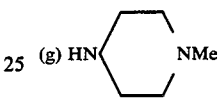NMe with 0.05M I$_2$ in a solution of the corresponding amine (10 percent) and tetrahydrofuran (THF) for 5 min. The product amidates were removed from the solid support (50 percent conc. ammonium hydroxide (NH$_4$OH)/Dioxane, 8 hrs., r.t.) and evaporated. $^{31}$P NMR spectra of both products show the presence of approximately equal amounts of diasteriormers ($^{31}$P NMR spectra were obtained in CDCl$_3$ and chemical shifts are reported relative to 5 percent phosphoric acid/D$_2$O (ext. std.); 2e δ-9.1, -8.8 ppm; 2f δ-7.9, -7.6 ppm.). The oxidation of H-phosphonate diesters to phosphoramidates is complicated by competitive hydrolysis, generating the phosphate diester 2a. Carbon tetrachloride (CCl$_4$) oxidation of H-phosphonate diesters to phosphoramidates (Atherton et al., J. Chem. Soc. 660 (1945), Zwierzak, A., Synthesis 507 (1975)) offers the advantage of low water solubility into CCl$_4$. All dinucleotide phosphoramidates (2b-g) were prepared with a 10 percent solution of the corresponding amine in CCl$_4$ (5 min) (A saturated solution of ammonia or methyl amine in Dioxane/CCl$_4$ ($\frac{1}{4}$) was used to prepare the corresponding phosphoramidates). High performance liquid chromatography (HPLC) of the samples indicate a high yield of product phosphoramidate with very little competitive hydrolysis (<3 percent dithymidine phosphate diester, 2a).

The stability of the phosphoramidate linkage to conc. NH$_4$OH was examined for each and the results indicate the phosphoramidates 2c-g are stable to the conditions necessary for removal of the common heterocyclic N-acyl protecting groups (55° C., 5 hrs). The phosphoramidate 2b rapidly decomposes under these conditions (t$_\frac{1}{2}$ ~15 min) to a mixture of the 3' and 5' phosphoramic acid monoesters (Tomasz, J., Nucleosides and Nucleotides 2, 51 (1983)). The stability of the dinucleotide phosphoramidates (2b-g) to enzymatic degradation by exonucleases was examined using spleen phosphodiesterase and snake venom phosphodiesterase. Incubation of the dinucleotides (2a-g) with the corresponding enzyme/buffer solution at 37° C. for 1 hr led to complete degradation of the phosphate diester (2a) with no detectable degradation of the phosphoramidates 2b–g (assessed via reverse phase HPLC). The observed enzymatic stability of the dinucleotide phosphoramidate 2b is contrary to the claims of Ogilvie (Nemer et al., Tetrahedron Lett. 21, 4149 (1980)) but is in agreement with those reported by Ietsinger (Letsinger et al., Nucl. Acids Res. 14, 3487 (1986)).

To further explore the scope of this oxidation procedure, undecathymidylic acid ($T_{11}$) was prepared containing from 1 to 9 phosphormorpholidate linkages. The synthesis of polythymidine H-phosphonate on controlled pore glass was carried out using the synthetic protocol described above. The strategy outlined in Scheme 4 demonstrates the synthesis of $T_{11}$ containing nine phosphormorpholidate linkages followed by one phosphate diester linkage. This strategy was used for all $T_{11}$ products containing 3' phosphoramidate linkages.

SCHEME 4
Synthesis of $T_{11}$ containing nine phosphormorpholidate linkages (3' end) followed by one phosphate diester linkage (5' end).
*indicates phosphormorpholidate linkage

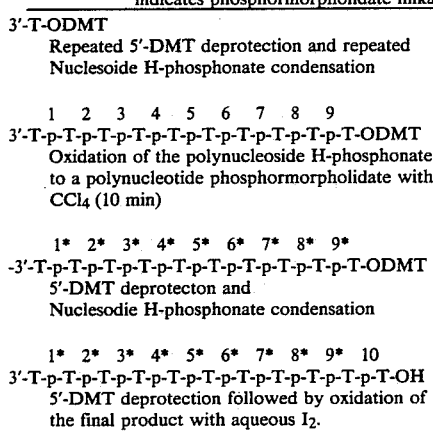

The products were removed from the solid support with conc. NH$_4$OH (2 hr/r.t.) and evaporated. Polyacrylamide gel electrophoresis (PAGE) and U.V. shadowing indicated a major product band with each. The band was cut, crushed, eluted with H$_2$O and isolated by reverse phase HPLC ($C_{18}$). An autoradiogram was derived from 5'-end labeling of these products with T4 polynucleotide kinase and $\gamma$-$^{32}$P ATP followed by PAGE (17 percent polyacrylamide/7M urea). The change in electrophoretic mobility of the different $T_{11}$ products was very pronounced, each additional morpholidate resulting in an increase in mass and a decrease in charge. It is interesting to note that the electrophoretic mobilities of the different $T_{11}$ products do not follow a strict mass/charge ratio dependence. The products containing many phosphoramidate linkages (high mass/charge ratio) have greater mobility than would be predicted based upon the mobilities of the $T_{11}$ products with fewer phosphoramidates. Treatment of each of these polythymidine phosphormorpholidates with 85 percent formic acid (95° C. 15 min) generated $T_{11}$ containing all diester linkages.

Nucleoside H-phosphonate diesters have been used as precursors to thiophosphate analogues (Fujii et al., Tetrahedron Lett. 26, 935 (1986)). This conversion is accomplished in high yield (>98 percent) directly from the polymer bound oligonucleoside H-phosphonate diester (1) by treatment with a solution of 0.1M S$_8$ in Triethylamine (TEA)/carbon disulfide (1/9, 5 min). In order to prepare radioisotopically labelled oligonucleotides having extremely high specific activity for use as hybridization probes, the S$_8$ that is employed will contain a proportion of $^{35}$S radioisotope.

Triesters of oxygen are prepared by reaction of oligonucleoside H-phosphonates (1) with a 10 percent solution of the corresponding alkanol (ROH) in N-methyl imidazole/TEA/CCl$_4$ (5/5/90) R is aryl, alkyl, heteroalkyl or heteroaryl generally having less than 10 carbon atoms, preferably MeOH or n-BuOH. This reaction is very susceptible to competitive hydrolysis and care must be taken to assure anhydrous conditions.

The primary and secondary amines (b)–(g) are to be considered merely representative. It is within the scope herein to employ substituents having the general formula

wherein X and Y are the same or different and are selected from the group of hydrogen, alkyl, heteroalkyl, heteroaryl or aryl, or are taken together to form a cycloalkene, cycloalkane or heterocycle. The species in which X or Y are, or are conjugated to form heteroalkyl and heteroaryl substituents are preferred for use as in vitro hybridization probes, whereas the alkyl or aryl substituents are preferred for in vivo hybridization.

The heteroatom in heteroaryl ROH, X or Y is selected from the group of S, N or O. about from 1 to 5 of which are present in the heteroaryl group. Heteroaryl species that are particularly useful in in vitro diagnostics are those in which the heteroaryl group is fluorescent, for example, rare earth metal chelates for use in pulsed fluorescence, or other known substituents for use in polarized fluorescence hybridization assays. Such fluorescent labelled oligonucleotides are particularly useful in hybridization assays because it is possible to conduct the assays without a phase separation by detecting changes in fluorescence upon hybridization to the target DNA, e.g. changes in polarization, emission wavelength absorption wavelength emission intensity and the like. The method herein facilitates the preparation of oligonucleotides which are heavily substituted with such fluorescent species and accordingly exhibit high specific activity.

The results presented above demonstrate that polynucleoside H-phosphonates are valuable precursors to a variety of internucleotide phosphate analogues. Oxidation of a polynucleoside H-phosphonate in the presence of amines leads to the corresponding polynucleotide phosphoramidate in high yield. The H-phosphonate method of DNA synthesis is a simple, fast and reagent efficient procedure that can now be applied to the rapid synthesis of DNA containing internucleotide phosphate analogues. This method provides an easy and efficient route to a variety of internucleotide phosphate analogues of DNA containing the naturally occurring nucleotides.

We claim:

1. A process for the synthesis of a polyribonucleotide or polydeoxyribonucleotide comprising (a) contacting a carrier-bound ribonucleotide or deoxyribonucleotide with a ribonucleoside H-phosphonate or deoxyribonucleotide H-phosphonate in the presence of an acylating agent under conditions for condensing the carrier-bound ribonucleotide or deoxyribonucleotide with the ribonucleoside H-phosphonate or deoxyribonucleoside H-phosphonate, wherein a hydroxyl of the ribonucleoside H-phosphonate or deoxynucleoside H-phosphonate is substituted with a blocking group for restricting the condensation reaction to the carrier-bound ribonucleotide or deoxyribonucleotide, (b) removing the blocking group from the ribonucleotide or deoxyribonucleotide hydroxyl, and (c) sequentially repeating steps (a) and (b) until a polynucleotide H-phosphonate having greater than two nucleotides has been obtained.

2. The method of claim 1 wherein the dehydrating agent is an organic acid halide.

3. The method of claim 1 wherein the acylating agent is an acid chloride.

4. The method of claim 1 wherein the step (d) occurs only after the entire polynucleotide H-phosphonate has been synthesized.

5. The process of claim 1 wherein the carrier is a polymer covalently bonded to the 3'-hydroxyl of the ribonucleotide or deoxyribonucleotide.

6. The process of claim 5 wherein the carrier is selected form the group consisting of controlled pore glass, silica gel and polystyrene.

7. The process of claim 1 further comprising contacting the polynucleotide H-phosphonate with an oxidizing agent capable of oxidizing the H-phosphonate moiety.

8. The process of claim 7 wherein the oxidizing agent is selected from the group consisting of aqueous iodine, N-chlorosuccinimide, N-bromosuccinimide, and a salt of periodic acid.

9. The process of claim 7 wherein the polynucleotide H-phosphonate is contacted with ROH, wherein R is alkyl, aryl, or heteroaryl containing from 1 to 5 S, N or O atoms and less than 10 carbon atoms, under conditions for producing an internucleotide triester.

10. The process of claim 9 wherein the heteroaryl group is fluorescent.

11. The process of claim 7 wherein the polynucleotide H-phosphonate is contacted with $S_8$ under conditions for producing an internucleotide thiophosphate.

12. A compound having the formula

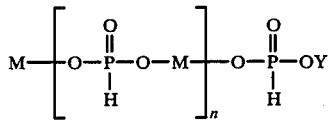

wherein Y is a positively charged counterion, n is $\geq 1$, M is a ribonucleoside or deoxyribonucleoside, and the ribonucleosides or deoxyrobonucleoside are covalently linked through their 5' and 3' hydroxyl groups.

13. The compound of claim 12 wherein M is a blocked nucleoside.

14. The compound of claim 12 wherein the blocking group is a dialkyl formamidine.

15. A process for the synthesis of a polyribonucleotide or polydeoxyribonucleotide comprising (a) contacting a carrier-bound ribonucleotide or deoxyribonucleotide with a ribonucleoside H-phosphonate or deoxyribonucleotide H-phosphonate in the presence of an acylating agent under conditions for condensing the carrier-bound ribonucleotide or deoxyribonucleotide with the ribonucleoside H-phosphonate or deoxyribonucleoside H-phosphonate;

wherein the acylating agent has the structure

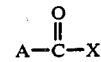

wherein A is selected form the group consisting of aryl, heteroaryl, and tertiary alkyl, the tertiary carbon being bonded directly to the carbonyl carbon, and wherein X is halogen or pseudohalogen; and wherein a hydroxyl of the ribonucleoside H-phosphonate or deoxynucleoside H-phosphonate is substituted with a blocking group for restricting the condensation reaction to the carrier-bound ribonucleotide or deoxyribonucleotide, (b) removing the blocking group from the ribonucleotide or deoxyribonucleotide hydroxyl, and (c) sequentially repeating steps (a) and (b) until a polynucleotide H-phosphonate having greater than two nucleotides has been obtained.

16. The method of claim 15 wherein the tertiary alkyl has the structure

in which R is the same or different normal or branched selected from the group consisting of alkyl, heteroalkyl, aryl and heteroaryl.

17. The method of claim 16 wherein X is chloride.

18. The method of claim 15 wherein the acylating agent is an acyl halide having a tertiary carbon bonded directly to the acyl carbon.

19. The method of claim 18 wherein the acylating agent is pivaloyl chloride.

20. The process of claim 15 wherein the carrier is a polymer covalently bonded to the 3'-hydroxyl of the ribonucleotide or deoxyribonucleotide.

21. The process of claim 20 wherein the carrier is selected from the group consisting of controlled pore glass, silica gel and polystyrene.

22. The process of claim 15 further comprising contacting the polynucleotide H-phosphonate with an oxidizing agent capable of oxidizing the H-phosphonate moiety.

23. The process of claim 22 wherein the oxidizing agent is selected from the group consisting of aqueous iodine, N-chlorosuccinimide, N-bromosuccinimide, and a salt of periodic acid.

24. The process of claim 22 wherein the polynucleotide H-phosphonate is contacted with ROH, wherein R is alkyl, aryl, or heteroaryl containing from 1 to 5 S, N or O atoms and less than 10 carbon atoms, under conditions for producing an internucleotide triester.

25. The process of claim 24 wherein the heteroaryl group is fluorescent.

* * * * *

UNITED STATES PATENT AND TRADEMARK OFFICE
CERTIFICATE OF CORRECTION

PATENT NO. : 4,959,463
DATED : Sept. 25, 1990
INVENTOR(S) : Brian C. Froehler & Mark D. Matteucci It is certified that error appears in the above-identified patent and that said Letters Patent is hereby corrected as shown below:

Column 15, line 11, "dehydrating" should read -- acylating --.

Signed and Sealed this

Sixth Day of July, 1993

Attest:

MICHAEL K. KIRK

Attesting Officer

Acting Commissioner of Patents and Trademarks